(12) United States Patent
Weiner et al.

(10) Patent No.: US 10,011,655 B2
(45) Date of Patent: Jul. 3, 2018

(54) COMPOSITIONS AND METHODS FOR THE IDENTIFICATION AND ISOLATION OF CELL-MEMBRANE PROTEIN SPECIFIC BINDING MOIETIES

(71) Applicant: AxioMx, Inc., Branford, CT (US)

(72) Inventors: Michael Weiner, Branford, CT (US); Margaret Kiss, Westbrook, CT (US)

(73) Assignee: AxioMx, Inc., Branford, CT (US)

( * ) Notice: Subject to any disclaimer, the term of this patent is extended or adjusted under 35 U.S.C. 154(b) by 22 days.

(21) Appl. No.: 14/652,385

(22) PCT Filed: Dec. 19, 2013

(86) PCT No.: PCT/US2013/076580
§ 371 (c)(1),
(2) Date: Jun. 15, 2015

(87) PCT Pub. No.: WO2014/100419
PCT Pub. Date: Jun. 26, 2014

(65) Prior Publication Data
US 2015/0322150 A1    Nov. 12, 2015

Related U.S. Application Data

(60) Provisional application No. 61/740,375, filed on Dec. 20, 2012.

(51) Int. Cl.
*C07K 16/28* (2006.01)
*C07K 1/14* (2006.01)
*G01N 33/68* (2006.01)

(52) U.S. Cl.
CPC ............... *C07K 16/28* (2013.01); *C07K 1/14* (2013.01); *G01N 33/6845* (2013.01); *C07K 2317/622* (2013.01)

(58) Field of Classification Search
CPC .... C07K 16/28; C07K 1/14; C07K 2317/622; G01N 33/6845
See application file for complete search history.

(56) References Cited

U.S. PATENT DOCUMENTS

| 2010/0210473 A1 | 8/2010 | Bowley et al. |
| 2011/0166027 A1 | 7/2011 | Weiner |
| 2012/0010107 A1 | 1/2012 | Griffiths et al. |

FOREIGN PATENT DOCUMENTS

| WO | WO-2010/129541 A1 | 11/2010 |
| WO | WO-2014/100419 A1 | 6/2014 |
| WO | WO-2014/134166 A9 | 9/2014 |
| WO | WO-2015/085079 A2 | 6/2015 |

OTHER PUBLICATIONS

U.S. Appl. No. 61/740,375, Weiner et al.
Benhar et al., "Highly efficient selection of phage antibodies mediated by display of antigen as Lpp-OmpA' fusions on live bacteria," J Mol Biol. 301(4):893-904 (2000).
Brouzes et al., "Droplet microfluidic technology for single-cell high-throughput screening," Proc Natl Acad Sci U S A. 106(34):14195-200 (2009).
Buhr et al., "Use of micro-emulsion technology for the directed evolution of antibodies," Methods. 58(1):28-33 (2012) (6 pages).
Deller et al., "Cell surface receptors," Curr Opin Struct Biol. 10(2):213-9 (2000).
Gebauer et al., "Engineered protein scaffolds as next-generation antibody therapeutics," Curr Opin Chem Biol. 13(3):245-55 (2009).
Ghadessy et al., "Directed evolution of polymerase function by compartmentalized self-replication," Proc Natl Acad Sci U S A. 98(8):4552-7 (2001).
Hegmans et al., "A model system for optimising the selection of membrane antigen-specific human antibodies on intact cells using phage antibody display technology," J Immunol Methods. 262(1-2):191-204 (2002).
Hoogenboom et al., "Antibody phage display technology and its applications," Immunotechnology. 4(1):1-20 (1998).
International Search Report and Written Opinion for International Patent Application No. PCT/US13/76580, dated Mar. 4, 2014 (16 pages).
Jakobsen et al., "Phage display-derived human monoclonal antibodies isolated by binding to the surface of live primary breast cancer cells recognize GRP78," Cancer Res. 67(19):9507-17 (2007).
Kiss et al., "Phage ESCape: an emulsion-based approach for the selection of recombinant phage display antibodies," J Immunol Methods. 367(1-2):17-26 (2011).
Koester et al., "Drop-based microfluidic devices for encapsulation of single cells," Lab Chip. 8(7):1110-5 (2008).
Labrijn et al., "Novel strategy for the selection of human recombinant Fab fragments to membrane proteins from a phage-display library," J Immunol Methods. 261(1-2):37-48 (2002).
Lee et al., "Bivalent antibody phage display mimics natural immunoglobulin," J Immunol Methods. 284(1-2): 119-32 (2004).
Lewerenz et al., "The cystine/glutamate antiporter system x(c)(−) in health and disease: from molecular mechanisms to novel therapeutic opportunities," Antioxid Redox Signal. 18(5):522-55 (2013).
Lo et al., "The x(c)-cystine/glutamate antiporter: a potential target for therapy of cancer and other diseases," J Cell Physiol. 215(3):593-602 (2008).
Marks et al., "By-passing immunization. Human antibodies from V-gene libraries displayed on phage," J Mol Biol. 222(3): 581-97 (1991).
Molek et al., "Peptide phage display as a tool for drug discovery: targeting membrane receptors," Molecules. 16(1):857-87 (2011).

(Continued)

*Primary Examiner* — Andrea S Grossman
(74) *Attorney, Agent, or Firm* — Clark & Elbing LLP (57) ABSTRACT

Disclosed are methods of identifying binding moieties that recognize antigens displayed on cells, such as membrane proteins or recombinant proteins that display eptiopes on the surface of cells. Binding moieties capable of binding membrane proteins can be difficult to obtain because these proteins can depend on their native environments for structural integrity. In some methods scFv phage display libraries are panned against whole cells expressing a membrane protein in an emulsion. Certain methods further permit discrimination of binding moieties according to their affinity or avidity for a target. This approach allows rapid identification of cell surface epitope specific antibodies for research, diagnostics, and immunotherapeutics.

11 Claims, 4 Drawing Sheets

(56) References Cited

OTHER PUBLICATIONS

Nie et al., "Identification of tumor associated single-chain Fv by panning and screening antibody phage library using tumor cells," World J Gastroenterol. 8(4):619-23 (2002), <http://www.wjgnet.com/1007-9327/full/v8i4/619.htm> retrieved on Jun. 19, 2015 (10 pages).

Palmer et al., "Selection of antibodies to cell surface determinants on mouse thymic epithelial cells using a phage display library," Immunology. 91(3):473-8 (1997).

Pampliega et al., "Increased expression of cystine/glutamate antiporter in multiple sclerosis," J Neuroinflammation. 8:63 (2011) (12 pages).

Popkov et al., "Isolation of human prostate cancer cell reactive antibodies using phage display technology," J Immunol Methods. 291(1-2):137-51 (2004).

Schofield et al., "Application of phage display to high throughput antibody generation and characterization," Genome Biol. 8(11):R254-R254.18 (2007).

Sepp et al., "Microbead display by in vitro compartmentalisation: selection for binding using flow cytometry," FEBS Lett. 532(3):455-8 (2002).

Shadidi et al., "An anti-leukemic single chain Fv antibody selected from a synthetic human phage antibody library," Biochem Biophys Res Commun. 280(2):548-52 (2001).

Sheets et al., "Efficient construction of a large nonimmune phage antibody library: the production of high-affinity human single-chain antibodies to protein antigens," Proc Natl Acad Sci U S A. 95(11):6157-62 (1998).

Shih et al., "xCt cystine transporter expression in HEK293 cells: pharmacology and localization," Biochem Biophys Res Commun. 282(5):1132-7 (2001).

Shukla et al., "Phage display selection for cell-specific ligands: development of a screening procedure suitable for small tumor specimens," J Drug Target. 13(1):7-18 (2005).

Siva et al., "Selection of anti-cancer antibodies from combinatorial libraries by whole-cell panning and stringent subtraction with human blood cells," J Immunol Methods. 330(1-2):109-19 (2008).

Smith, "Filamentous fusion phage: novel expression vectors that display cloned antigens on the virion surface," Science. 228(4705):1315-7 (1985).

Tate, "Overexpression of mammalian integral membrane proteins for structural studies," FEBS Lett. 504(3):94-8 (2001).

Tur et al., "An anti-GD2 single chain Fv selected by phage display and fused to Pseudomonas exotoxin A develops specific cytotoxic activity against neuroblastoma derived cell lines," Int J Mol Med. 8(5):579-84 (2001).

Wang et al., "Selection of CC chemokine receptor 5-binding peptide from a phage display peptide library," Biosci Biotechnol Biochem. 70(9):2035-41 (2006).

Watters et al., "An optimized method for cell-based phage display panning," Immunotechnology. 3(1):21-9 (1997).

Williams et al., "Generation of anti-colorectal cancer fab phage display libraries with a high percentage of diverse antigen-reactive clones," Comb Chem High Throughput Screen. 5(6):489-99 (2002).

Wittrup, "Protein engineering by cell-surface display," Curr Opin Biotechnol. 12(4):395-9 (2001).

Zhang et al., "Neuroblastoma tumor cell-binding peptides identified through random peptide phage display," Cancer Lett. 171(2):153-64 (2001).

Gadeberg et al., "Cytotoxic effect of an alpha-hemolytic *Escherichia coli* strain on human blood monocytes and granulocytes in vitro," Infect Immun. 41(1):358-64 (1983).

Sharifi et al., "Studying the effect of LPS on cytotoxicity and apoptosis in PC12 neuronal cells: Role of Bax, Bcl-2, and Caspase-3 protein expression," Toxicol Mech Methods. 20(6):316-320 (2010).

Extended European Search Report for European Application No. 13865627.7, dated Jul. 11, 2016 (10 pages).

Mutuberria et al., "Model systems to study the parameters determining the success of phage antibody selections on complex antigens," J Immunol Methods. 231(1-2):65-81 (1999).

COMPOSITIONS AND METHODS FOR THE IDENTIFICATION AND ISOLATION OF CELL-MEMBRANE PROTEIN SPECIFIC BINDING MOIETIES

CROSS-REFERENCE TO RELATED APPLICATIONS

This application claims the benefit of U.S. Provisional Application No. 61/740,375, filed Dec. 20, 2012, which is hereby incorporated by reference in its entirety.

BACKGROUND OF THE INVENTION

Plasma membrane-embedded receptors serve as biomarkers for many human diseases and represent more than 50% of drug targets (Molek et al., 2011. Peptide phage display as a tool for drug discovery: targeting membrane receptors. *Molecules* 16, 857-887). There is a demand in research, diagnostics, and therapeutics for affinity reagents that recognize this class of molecules, but antibodies against membrane proteins can be difficult to obtain. This is because these proteins strongly rely on their native environment for structural integrity, and they often contain glycosylation and other post-translational modifications. Affinity reagents, such as antibodies, are needed to study protein expression patterns, sub-cellular localization, and post-translational modifications in cells and tissues. Traditionally, producing an antibody to a particular protein requires immunization of animals and recovery of antibodies from their sera. In contrast, newer methods have been developed that involve the generation of large libraries of either recombinant antibodies or other affinity scaffolds that are engineered to bind target molecules, and then screening these libraries in vitro for binding moieties having desired binding properties.

Phage display a widely used method for selecting binding molecules from recombinant antibody libraries (Lee et al., 2004. Bivalent antibody phage display mimics natural immunoglobulin. *J. Immunol. Methods* 284: 119-132; Marks et al., 1991. By-passing immunization. Human antibodies from V-gene libraries displayed on phage. *J. Mol. Biol.* 222: 581-597; Schofield et al., 2007. Application of phage display to high throughput antibody generation and characterization. *Genome Biol.* 8: R254; Sheets et al., 1998. Efficient construction of a large nonimmune phage antibody library: the production of high-affinity human single-chain antibodies to protein antigens. *Proc. Natl. Acad. Sci. USA* 95: 6157-6162). Since no immunization steps are required, comprehensive phage-antibody libraries permit in vitro targeting of antigens which are known to be toxic or possess low antigenicity in vivo. In addition, the DNA encoding the antibody is accessible in phage display, providing not only the antibody sequence, but facilitating cloning and engineering of the protein in many ways. High affinity phage antibodies have been selected against numerous cellular proteins and small molecules (Hoogenboom et al., 1998. Antibody phage display technology and its applications. *Immunotechnology* 4: 1-20).

Traditional methods of phage display panning involve the selection of phage display libraries against purified antigen immobilized to a solid surface. These methods may not be directly applicable to some antigens, such as membrane proteins, which may require native environments to achieve a particular structure (Deller et al., 2000. Cell surface receptors. *Curr. Opin. Struct. Biol.* 10, 213-219; Tate, C. G. 2001. Overexpression of mammalian integral membrane proteins for structural studies. *FEBS Lett.* 504, 94-98). As an alternative to selection against single protein products, several groups have panned phage libraries directly against affected tissue or whole cells (Watters et al., 1997. An optimized method for cell-based Phage display panning. *Immunotechnology* 3: 21-39; Nie et al., 2002. Identification of tumor-associated single-chain Fv by panning and screening antibody phage library using tumor cells. *World J. Gastroenterol.* 8: 619-623; Williams et al., 2002. Generation of anti-colorectal cancer fab phage display libraries with a high percentage of diverse antigen-reactive clones. *Comb. Chem. High Throughput Screen* 5: 489-499; Zhang et al., 2001. Neuroblastoma tumor cell-binding peptides identified through random peptide phage display. *Cancer Lett.* 171: 153-164; Tur et al., 2001. An anti-GD2 single chain Fv selected by phage display and fused to Pseudomonas exotoxin A develops specific cytotoxic activity against neuroblastoma derived cell lines. *Int. J. Mol. Med.* 8: 579-584; Hegmans et al., 2002. A model system for optimising the selection of membrane antigen-specific human antibodies on intact cells using phage antibody display technology. *J. Immunol. Methods* 262: 191-204; Labrijn et al., 2002. Novel strategy for the selection of human recombinant Fab fragments to membrane proteins from a phage-display library. *J. Immunol. Methods* 261: 37-48; Shadidi et al., 2001. An anti-leukemic single chain Fv antibody selected from a synthetic human phage antibody library. *Biochem. Biophys. Res. Commun.* 280: 548-552). Since cell-surface antigens may have complex conformational constraints, such as multiple membrane-spanning domains or protein interaction domains, in addition to glycosylation and other post-translational modifications, whole cell biopanning eliminates certain concerns regarding target protein structure, allowing selection against the extracellular regions of receptors in their native conformations. Such protocols can be employed, e.g., with live or fixed cells (Shukla et al., 2005. Phage display selection for cell-specific ligands: development of a screening procedure suitable for small tumor specimens. *J. Drug Targeting* 13: 7-18; Jakobsen et al., 2007. Phage display derived human monoclonal antibodies isolated by binding to the surface of live primary breast cancer cells recognize GRP78. *Cancer Research* 67: 9507; Wang et al., 2006. Selection of CC Chemokine receptor 5-binding peptide from a phage display peptide library. *Biosci. Biotechnol. Biochem.* 70, 2035-2041; Hoffman et al., 2004. In vivo and ex vivo selections using phage-displayed libraries. In *Phage Display: A practical approach*, Lowman, H. B., Clackson, T., Eds., Oxford University Press, New York, N.Y., 171-192). Since the plasma membrane is extremely complex, with diverse protein and carbohydrate structures that may complicate affinity selections using phage display libraries, subtractive panning against similar but not identical cells may be used to limit the recovery of binding moieties interacting with non-target cell surface molecules (Palmer et al., 1997. Selection of antibodies to cell surface determinants on mouse thymic epithelial cells using a phage display library. *Immunology* 91, 473; Popkov et al., 2004. Isolation of human prostate cancer cell reactive antibodies using phage display technology. *J. Immunol. Methods* 291, 137; Siva et al., 2008. Selection of anti-cancer antibodies from combinatorial libraries by whole-cell panning and stringent subtraction with human blood cells. *J. Immunol. Methods* 330, 109-119).

Despite the advantages of whole cell panning for the isolation of antibodies against cell-surface markers, conventional cell-based biopanning approaches can suffer from several limitations (Hoffman et al., 2004. Phage display: A practical approach. eds. T. Clackson and H. Lowman.

Oxford University Press, Oxford, United Kingdom, p. 171-192). Each round of biopanning typically requires a relatively large number of cells ($10^5$-$10^7$), making the technique difficult to apply to small cell populations harvested from organs and tissues. In addition, the wash steps are often inefficient at removing nonspecifically or weakly bound phage. Repeated stringent washes, on the other hand, can lead to loss of cells and, consequently, potential antibody-displaying phage that are bound to them.

SUMMARY OF THE INVENTION

In general, the invention features identification of binding moieties that specifically bind cell-membrane bound epitopes. These methods include contacting, within individual droplets of a microemulsion, cells having a particular cell-membrane bound epitope with candidate binding moieties. When complexes are formed between binding moieties and cells within individual droplets, the droplet-containing emulsion can be broken and the cell-membrane epitope specific binding moieties can be isolated. Throughout these methods, the binding moieties can, e.g., be proteins expressed on the surfaces of viruses (e.g., phage) or cells (e.g., bacterial or yeast cells). Such expression permits isolation of the binding moiety with a corresponding nucleic acid that encodes the binding moiety. This permits rapid expansion and, e.g., mutagenesis of candidate binding moieties.

This method allows us to individually query clonal populations of amplified phage against an antigen and select phage capable of binding the antigen via, e.g., Fluorescence Activated Cell Sorting (FACS). In one example, HEK-293 cells are used which over-express the ErbB2 (Her2) receptor and phage displaying an anti-Her2 scFv.

The use of emulsions to generate microdroplets offers advantages for cell-based panning. Smaller volumes (fewer cells) are required, facilitating identification of specific binders from a single round of selection (Buhr et al., 2012. Use of micro-emulsion technology for the directed evolution of antibodies. *Methods* 58: 28-33; Becher, P. (1957) Emulsions: theory and practice. Reinhold Publishing; Sherman, P. (1968) Emulsion science. Academic Press, London. Smith, GP (1985) Science, 228, 1315-7; Lissant, K J, ed Emulsions and emulsion technology. Surfactant Science New York: Marcel Dekker, 1974; Sepp et al., 2002. Microbead display by in vitro compartmentalisation: selection for binding using flow cytometry. *FEBS Lett.* 532: 455-8; Ghadessy et al., 2001. Directed evolution of polymerase function by compartmentalized self-replication. *Proc. Natl. Acad. Sci. USA* 98: 4552-7; Kiss et al., 2011. Phage ESCape: an emulsion-based approach for the selection of recombinant phage display antibodies. *J. Immunol. Methods* 367: 17-26). Since clonal populations of antibody-displaying phage are individually interrogated against the cell displaying the antigen, specific binders should be enriched on the cell surface compared to weak or non-specific ones, permitting discrimination of high affinity binders by FACS.

In a first aspect, the present invention is a method of isolating a binding moiety specific to a cell-membrane bound epitope, the method including a first step of providing an emulsion with a plurality of droplets, followed by a second step of contacting, within the droplets, one or more antigen carriers displaying the cell-membrane bound epitope with a plurality of binding moiety carriers, wherein, if an individual binding moiety is specific to the antigen carrier present in the same droplet, the contacting results in a complex. This aspect of the invention further includes a third step of breaking the emulsion, a fourth step of washing the complexes, a fifth step of adding a labeled binding agent specific for the binding moiety carrier to the washed complexes resulting in the labeling of the complexes, and a sixth step of isolating the labeled complexes. The last step results in the isolation of a binding moiety specific for the cell-membrane bound epitope. Any embodiment of the present invention may further include repeating the steps of this aspect with a plurality of binding moieties isolated by this last step.

In certain embodiments, the binding moiety carrier is a virus or cell. In particular embodiments, the binding moiety carrier is a lambda phage, T4 phage, T7 phage, yeast cell, or bacterial cell. In any of these embodiments, the virus or cell can include a DARPin, FN3 (fibronectin repeats), Fork-head associate protein, scFv, Fab, or other antibody-derived protein.

In any of the above embodiments, the binding moiety carrier can be released into the individual droplet by virus-transduced bacteria. In particular embodiments, the virus-transduced bacteria are phage-transduced bacteria.

In any of the above embodiments, the labeled binding agent can be a fluorescent label. In such embodiments, the step of isolating the labeled complexes occurs by fluorescent activated cell sorting (FACS). In any of the above embodiments, the cell-membrane bound epitope can be recombinantly expressed by the cells. In any of the above embodiments, the cell-membrane bound epitope can be natively expressed by the cells.

In particular embodiments of the present invention, the plurality of binding moiety carriers of the second step are generated by contacting cells not having the cell-membrane bound epitope with a plurality of binding moieties and washing the cells, thereby forming a mixture of binding moiety carriers that failed to bind the cells not having the cell-membrane bound epitope, and isolating the mixture of binding moiety carriers, thereby generating the plurality of binding moieties of the second step.

In any of the above embodiments, the emulsion can be a monodispersed emulsion or heterodispersed emulsion.

"Binding moiety" means a protein or polypeptide, or a fragment thereof, capable of binding an antigen, such as an antigen displayed on the surface of a cell. A particular binding moiety is a cognate to an antigen if it is capable of binding a particular antigen or group of antigens. A cognate binding moiety and any antigen to which it binds is referred to as a "cognate pair." The binding of an antigen and cognate binding moiety is referred to as a "cognate pair interaction."

"Antibody" means any form of immunoglobulin, heavy chain antibody, light chain antibody, LRR-based antibody, or other protein scaffold with antibody-like properties, as well as any other immunological binding moiety known in the art, including antibody fragments (e.g., a Fab, Fab', Fab'2, F(ab')$_2$, Fd, Fv, Feb, scFv, or SMIP). The subunit structures and three-dimensional configurations of different classes of antibodies are known in the art.

"Antibody fragment" means a binding moiety that includes a portion derived from or having significant homology to an antibody, such as the antigen-binding portion of an antibody.

"Displayed" protein or polypeptide means a protein or polypeptide having at least one amino acid present on the external surface of a cell, virus, or other biological entity or support, such that a molecule contacted with the external surface of the cell, virus, or other biological entity or support may directly interact with the protein or polypeptide.

"Cell membrane bound epitope" means a displayed protein or polypeptide having a structure or characteristic dependent upon interaction with the cellular membrane.

"Binding moiety carrier" means a cell or virus displaying a binding moiety.

"Antigen carrier" means a cell displaying an antigen.

"Complex" means a binding moiety carrier and an antigen carrier bound by interaction of an antigen and a cognate binding moiety.

BRIEF DESCRIPTION OF THE DRAWINGS

FIG. 1 is a schematic showing a workflow for the expression of synthesized nucleic acids. In one example of the use of this workflow, human the integral membrane protein Slc7A11 (xCT) and Slc7A9 amplified from cDNA clones and synthesized mouse xCT are sub-cloned into a mammalian expression vector. HEK-293 suspension cells are transiently transfected with the resultant expression constructs. The HEK-293 cells are assayed for over-expression of xCT using a commercial polyclonal antibody. If over-expression is not achieved initially, alternate expression vectors and cell lines can be employed.

FIG. 2 is a schematic showing steps of phage microemulsion for the identification of binding moieties. Within a microdroplet, phage-transduced *E. coli* attach to an antigen-coated bead or cell (SF9, yeast, mammalian, *Rhodobacter, Arabidopsis*, etc.) expressing a membrane spanning protein. After overnight incubation, the emulsion is broken, the beads or cells are washed, and a FITC-labeled anti-M13 antibody is added to detect bound phage. The beads or cells are then sorted by Fluorescence Activated Cell Sorting (FACS).

FIG. 3 is a schematic showing a workflow for the use of emulsion to identify lead candidate binding moieties. In one example of the use of this workflow, emulsion conditions can be established that support survival of the xCT-expressing cells and growth of phage-transduced *E. coli*. An scFv phage library (counter-selected against control cells) is screened against xCT-expressing cells in an emulsion, and the phage-bound cells are sorted by Fluorescence Activated Cell Sorting (FACS). This process is repeated for further enrichment as required. Individual phage clones are analyzed for specificity in a phage ELISA against fixed, immobilized cells. Enriched clones from the emulsion screen are affinity matured using our proprietary mutagenesis approach followed by conventional whole cell phage biopanning with reduced cells and increased wash stringency in each round of selection. Following maturation, ELISA-positive clones are expressed and purified in *E. coli*. The purified scFvs can be validated by FACS against the cell lines described in section 4.2.1. Validated scFvs can be tested for recognition of multiple epitopes by competition ELISA. If problems arise at any of the steps, alternative approaches are indicated.

FIG. 4 is a schematic showing a workflow for cloning $V_H$ and $V_L$ int vectors and purification of the resultant vectors. In one example of the use of this workflow, the $V_H$ and $V_L$ sequences can be amplified and cloned from lead scFvs into vectors expressing the constant regions of the heavy and light chains (InvivoGen cat # pFUSE2ss-CHIg-hG1 and pFUSE2ss-CLIg-hl2). The entire heavy and light chains can be amplified from the appropriate expression vectors and cloned into the Freedom pCHO 1.0 expression vector. Two expression plasmids are created with the heavy and light chain in different orientations and a small scale (50 mL culture) transient transfection is conducted to test which orientation yields the most functional protein. The proteins can be purified from the cell supernatant by affinity chromatography using protein A resin. Function against xCT can be verified by FACS using the over-expressing 293-F cell line. Based on the results of the small scale study, the transient transfections can be repeated and scale up to 2.5 L cultures to yield 50 mg of purified material.

DETAILED DESCRIPTION OF THE INVENTION

In general, the invention features identification of cognate binding moieties of cell-displayed antigens. These methods include contacting, within individual droplets of an emulsion, one or more cells displaying a membrane epitope with one or more binding moiety carriers. After complexes form between antigen and cognate binding moiety carriers within individual droplets, the emulsion can be broken and the cognate binding moiety carriers can be isolated. In various embodiments of the present invention, the binding moieties can, e.g., be displayed on the surfaces of viruses (e.g., phage) or cells (e.g., bacterial or yeast cells). Isolation of such binding moiety carriers constitutes isolation of both the binding moiety and the nucleic acid from which the binding moiety was expressed. This permits, e.g., rapid expansion and mutagenesis of candidate binding moieties.

Cells

A cell of the present invention may be any manipulable cell known in the art, such as a cell descending from a laboratory, commercial, or industrial cell line known in the art. The cell may be an archaeal cell, prokaryotic cell, bacterial cell, fungal cell, or eukaryotic cell. The cell may be a yeast cell, plant cell, or animal cell. In some instances, the cell may be an *E. coli* cell or *S. cerevisiae* cell. The cell may be, e.g., a mammalian cell such as a human cell. The cell may be an immortalized cell. Alternatively, the cell may be a non-immortalized cell. In particular embodiments, the cells may be HEK-293, 293-F, NIH3T3 fibroblasts, Sf9, TiNi, *Saccharomyces* sp., HeLa, *Rhodobacter, Arabidopsis*, murine hippocampal HT22, or astrocyte cells. A cell of the present invention can be engineered, e.g., to express a gene or protein that is not endogenous to the cell. More specifically, a cell of the present invention can be cell that is engineered to over-express an antigen protein, e.g., an antigen that is not endogenous to the cell. A cell of the present invention may display an antigen or binding moiety. Methods of engineering cells, e.g., to express a protein, over-express a protein, or display an antigen, are known in the art. Further, methods of optimizing cell lines for such use are also known in the art, and may be applied to the optimization of cell lines for use in the methods of the present invention. The cells of any embodiment of the present invention may be a mixed populations of cells. In particular embodiments of the present invention, the cells may be fixed.

Viruses

A virus of the present invention may be any manipulable virus known in the art, e.g., for laboratory, commercial, or industrial use. A virus of the present invention may be a virus known to be capable of infecting archaea, fungi, bacteria, or eukaryotes. A virus may be capable of infecting plants or animals. In some instances, the virus may be a virus known to infect *E. coli* cells or yeast cells. A virus may be a dsDNA virus, ssDNA virus, dsRNA virus, ssRNA virus, ssRNA-RT virus, or dsDNA-RT virus. For example, the virus may be a lentivirus, adenovirus, adeno-associated virus, baculovirus, measles virus, influenza virus, human immunodeficiency virus (HIV), arbovirus, cholera virus, chicken pox virus, dengue virus, diphtheria virus, hantavirus, herpes virus, Ebola virus, Marburg virus, parainfluenza virus, rabies virus, syphilis virus, bacteriophage, lambda bacteriophage, cytomegalovirus, Epstein Barr Virus (EBV), vaccinia virus, or other virus known in the art. A virus of the present invention may be, e.g., M13 bacteriophage. A virus of the present invention may further be a variant of a form known in the art.

A reaction of the present experiment may include one or more virus types and one or more types of cells. In such embodiments, the viruses and cells may be selected so that each virus type is capable of infecting one or more of the included types of cells. A virion of the present invention may display a binding moiety.

Antigens

An antigen of the present invention may be a protein or polypeptide to which a binding moiety may bind. An antigen of the present invention may be displayed on the surface of a cell. In some instances, an antigen of the present invention is a protein or polypeptide that is normally found on the surface of a cell. In some instances, an antigen is transgenic. In other instances, the antigen includes a protein or polypeptide that is not normally found on the surface of a cell. In certain instances, the antigen is a protein or polypeptide that is normally found within a cell, such as in the cytoplasm or an organelle. In certain instances, the antigen is a transgenic protein or polypeptide.

An antigen may be any natural or synthetic protein, e.g., a protein known in the art. An antigen may be a protein or peptide found in a protein or peptide database (e.g., SWISS-PROT, TrEMBL, SBASE, PFAM, or others known in the art), or a fragment or variant thereof. An antigen may be a protein or peptide that may be derived (e.g., by transcription and/or translation) from a nucleic acid sequence known in the art, such as a nucleic acid sequence found in a nucleic acid database (e.g., GenBank, TIGR, or others known in the art) or a fragment or variant thereof.

An antigen may be a protein or polypeptide endogenous to a pathogen, such as a protein or polypeptide selectively expressed or displayed by one or more cells of a pathogen. The pathogen may be, e.g., a virus, infectious bacteria, infectious fungus, or infectious eukaryote. For example, the pathogen may be *Burkholderia pseudomallei*. In some instances, the pathogen is a pathogen of one or more animal species, such as humans. Numerous pathogens are known in the art. In particular embodiments, a plurality of distinct antigens of the present invention is selected from a single pathogen. In particular embodiments, a plurality of distinct antigens of the present invention are selected from a plurality of distinct pathogens.

An antigen may be a protein or polypeptide associated with diseased cells or a disease state. For instance, an antigen may be a protein or polypeptide associated with cancer cells, such as a protein or polypeptide selectively expressed by cancer cells. In certain instances, the antigen is a tumor marker, i.e., a substance produced by a tumor or produced by a non-cancer cell in response to the presence of a tumor. Many tumor markers are not exclusively expressed by cancer cells, but may be expressed at elevated levels in cancerous cells or expressed at elevated levels in non-cancer cells in response to the presence of a tumor. The antigen may be a protein or polypeptide expressed in connection with any disease or condition known in the art.

An antigen may be a commercially valuable product, such as a protein or polypeptide for use in the treatment of a disease or disorder or useful as a research tool. In such instances, a cognate binding moiety of the antigen may be useful in the isolation of the antigen, e.g., for research or commercial purposes.

An antigen of the present invention may include one or more modified amino acids, such as a post-translationally modified amino acid. For example, one or more amino acids of an antigen of the present invention may be glycosylated, acetylated, amidated, formylated, gamma-carboxyglutamic acid hydroxylated, methylated, phosphorylated, sulfated, or modified with pyrrolidone carboxylic acid. An antigen amino acid may include one or more amino acids having a phosphoserine. An antigen of the present invention may include one or more amino acids having a phosphothreonine or phosphotyrosine modification.

In various embodiments of the present invention, the antigen may be a cell membrane bound epitope. In some instances of the present invention, a cell membrane bound epitope may be a known transmembrane protein, i.e., a protein known to have one or more transmembrane domains, a protein previously identified as associating with the cellular membrane, or a protein predicted to have one or more transmembrane domains by one or more methods of domain prediction known in the art. The cell membrane bound epitope may alternatively be a fragment of such a protein. A cell membrane bound epitope may be an integral membrane protein or peripheral membrane protein. Cell membrane bound epitopes include, without limitation, receptors, signaling proteins, transport proteins, cell adhesion proteins, and enzymes. Numerous particular members of these groups are known in the art. Other groups of membrane-associated proteins are known in the art, as are particular members of these groups. The cell membrane bound epitope me be a protein or polypeptide having a sequence present in nature, substantially similar to a sequence present in nature, engineered or otherwise modified from a sequence present in nature, or artificially generated, e.g., by techniques of molecular biology. In other instances, the cell membrane bound epitope may be a cellular product other than a protein or polypeptide.

The present invention may be applicable to any antigen protein or polypeptide that may be displayed on the surface of a cell. An antigen may be encoded by the cell on which it is displayed. In some instances, the antigen may be present in an antigen fusion protein.

Binding Moieties

A binding moiety of the present invention may be any protein or polypeptide capable of binding an antigen. In some instances, a binding moiety of the present invention includes a protein or polypeptide that is normally found on the surface of a virus. In some instances, a binding moiety is a transgenic binding moiety. In some instances, a binding moiety is an antibody, such as a whole antibody or an antibody fragment, such as an antigen-binding fragment.

An antibody of the present invention may be a whole antibody or immunoglobulin or an antibody fragment. An antibody may be multispecific, e.g., bispecific. An antibody of the present invention may be mammalian (e.g., human or mouse), humanized, chimeric, recombinant, synthetically produced, or naturally isolated.

In most mammals, including humans, whole antibodies have at least two heavy (H) chains and two light (L) chains connected by disulfide bonds. Each heavy chain consists of a heavy chain variable region ($V_H$) and a heavy chain constant region ($C_H$). The heavy chain constant region consists of three domains, $C_H1$, $C_H2$, and $C_H3$ and a hinge region between $C_H1$ and $C_H2$. Each light chain consists of a light chain variable region ($V_L$) and a light chain constant region. The light chain constant region consists of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Antibodies of the present invention include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, or a protein scaffold with antibody-like properties, such as fibronectin or ankyrin repeats. The antibody can have any of the following isotypes: IgG (e.g., IgG1, IgG2, IgG3, and IgG4), IgM, IgA (e.g., IgA1, IgA2, and IgAsec), IgD, or IgE.

An antibody fragment of the present invention may include one or more segments derived from an antibody. A segment derived from an antibody may retain the ability to specifically bind to a particular antigen. An antibody fragment may be, e.g., a Fab, Fab', Fab'2, F(ab')$_2$, Fd, Fv, Feb, scFv, or SMIP. An antibody fragment may be, e.g., a diabody, triabody, affibody, nanobody, aptamer, domain antibody, linear antibody, single-chain antibody, or multispecific antibodies formed from antibody fragments.

Examples of antibody fragments include: (i) a Fab fragment: a monovalent fragment consisting of $V_L$, $V_H$, $C_L$, and $C_H1$ domains; (ii) a F(ab')$_2$ fragment: a bivalent fragment including two Fab fragments linked by a disulfide bridge at the hinge region; (iii) a Fd fragment: a fragment consisting of $V_H$ and $C_H1$ domains; (iv) a Fv fragment: a fragment consisting of the $V_L$ and $V_H$ domains of a single arm of an antibody; (v) a dAb fragment: a fragment including $V_H$ and $V_L$ domains; (vi) a dAb fragment: a fragment consisting of a $V_H$ domain; (vii) a dAb fragment: a fragment consisting of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, e.g., by a synthetic linker that enables them to be made as a single protein chain in which the $V_L$ and $V_H$ regions pair to form monovalent molecules (known as single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more variable regions or constant regions derived from a first species and one or more variable regions or constant regions derived from a second species. Chimeric antibodies may be constructed, e.g., by genetic engineering. A chimeric antibody may include immunoglobulin gene segments belonging to different species (e.g., from a mouse and a human).

An antibody of the present invention may be a human antibody. A human antibody refers to a binding moiety having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, e.g., mutations. A variation or additional amino acid may be introduced, e.g., by human manipulation. A human antibody of the present invention is not chimeric.

An antibody of the present invention may be humanized, meaning that an antibody that includes one or more complementarity determining regions (e.g., at least one CDR) substantially derived from a non-human immunoglobulin or antibody is manipulated to include at least one immunoglobulin domain having a variable region that includes a variable framework region substantially derived from a human immunoglobulin or antibody.

In particular embodiments, one or more binding moieties of the present invention are antibodies derived from the sequence of an antibody expressed by a (e.g., a B-cell) cell of an inoculated subject. In particular embodiments, one or more binding moieties of the present invention are antibodies derived from the sequence of an antibody expressed by a naïve cell.

In certain embodiments of the present invention, a binding moiety is based on an alternative scaffold. Scaffolds based on different human or non-human proteins or protein domains are known in the art (see, e.g., Gebauer, M. & Skerra, A. Curr. Opin. Chem. Biol. 2009, 13:245-255). Different proteins have been investigated as frameworks, including affibodies, lipocalins, ankyrin-repeat proteins, natural peptide binding domains, enzymes, GFP, small disulfide-bonded peptides, protease inhibitors, and others.

A binding moiety of the present invention may be a protein or polypeptide that is not an antibody. A binding moiety may be, e.g., a kinase, a phosphatase, a proteasomal protein, a protein chaperone, a receptor (e.g., an innate immune receptor or signaling peptide receptor), a synbody, an artificial antibody, a protein having a thioredoxin fold (e.g., a disulfide isomerase, DsbA, glutaredoxin, glutathione S-transferase, calsequestrin, glutathione peroxidase, or glutathione peroxiredoxin), a protein having a fold derived from a thioredoxin fold, a repeat protein, a protein known to participate in a protein complex, a protein known in the art as a protein capable of participating in a protein-protein interaction, or any variant thereof (e.g., a variant that modifies the structure or binding properties thereof). A binding moiety of the present invention may be any protein or polypeptide having a protein binding domain known in the art, including any natural or synthetic protein that includes a protein binding domain. A binding moiety of the present invention may also be any protein or polypeptide having a polynucleotide binding domain known in the art, including any natural or synthetic protein that includes a polynucleotide binding domain.

In any embodiment of the present invention, a population of binding moiety-displaying virions may be subtracted prior to being contacted with cells displaying antigens of the present invention. For instance, a population of scFv-displaying virions can be subtracted against cells that do not display binding moieties of the present invention to remove non-specific binding moieties and binding moieties that bind non-target epitopes displayed by cells. In certain embodiments, a population of binding moiety-displaying virions is subtracted through two or more rounds of subtraction. Methods of subtraction are known in the art.

Fusion Proteins

An antigen or binding moiety of the present invention may be present in a fusion protein that enables display. In some instances, a binding moiety is present in a binding moiety fusion protein that further includes a segment that enables viral display. In some instances, an antigen is present in a binding moiety fusion protein that further includes a segment that enables cell surface display. A segment that enables display may be any polypeptide including a sequence of a known transmembrane domain or a sequence derived therefrom.

In one example, an antigen is fused to an F pilin protein (e.g., TraA) or a fragment thereof for expression on the surface of a bacterial cell, e.g., an *E. coli* cell. In particular instances, the fusion protein includes a segment without which the antigen would not be displayed.

In another example, an antigen is fused to the outer membrane protein OmpA or a fragment thereof. Such a fusion protein may further include one or more amino acids derived from the major outer membrane protein Lpp. In particular instances, expression of a fusion protein including Lpp-OmpA and an antigen in *E. coli* cells results in display the antigen. Lpp-OmpA fusion constructs are known in the art, e.g., in Benhar et al., 2000 *JMB* 301: 893-904, which is herein incorporated by reference.

Not all displayed antigens or displayed binding moieties of the present invention are fusion proteins.

Emulsions

Emulsion may be achieved by a variety of methods known in the art. In some embodiments, the emulsion is an emulsion that is stable to a denaturing temperature, e.g., to 95° C. or higher. An exemplary emulsion may be an oil and water emulsion. In some embodiments, the emulsion may be a perfluorcarbon oil emulsion. Other oil/surfactant mixtures, e.g., silicone oils, may also be utilized in particular embodiments. An emulsion may be a well or a plurality of wells in which one or more capture complexes are compartmentalized. Compartmentalization of capture complexes into wells may be achieved, in some embodiments, due to physical limitations relating to the mass or dimensions of the capture complexes, the dimensions of the well, or a combination thereof. A well may be a fiber-optic faceplate where the central core is etched with an acid, such as an acid to which the core-cladding is resistant. A well may be a molded well. The wells may be covered to prevent communication between the wells, such that the beads present in a particular well remain within the well or are inhibited from moving into a different well. The cover may be a solid sheet or physical barrier, such as a neoprene gasket, or a liquid barrier, such as perfluorocarbon oil. Methods applicable to the present invention are known in the art (e.g., Shukla et al., 2005. Phage display selection for cell-specific ligands: Development of a screening procedure suitable for small tumor specimens. *J. Drug Targeting* 13: 7-18; Koster et al., 2008. Drop-based microfluidic devices for encapsulation of single cells. *Lab on a Chip* 8: 1110-1115).

An emulsion of the present invention may be a monodisperse emulsion or heterodisperse emulsion. Each droplet in the emulsion may contain, or contain on average, 0-10 antigen carriers. For instances, a given droplet may contain 0, 1, 2, 3, 4, 5, 6, 7, 8, 9, or 10 antigen carriers. In particular embodiments, a given droplet may contain 0, 1, 2, or 3 antigen carriers. On average, the droplets of an emulsion of the present in invention may contain 0-3 antigen carriers, such as 0, 1, 2, or 3 antigen carriers, as rounded to the nearest whole number. In some embodiments, the number of antigen carriers in each emulsion droplet, on average, will be 1, or between 0 and 1, or between 1 and 2.

An emulsion of the present invention may be a monodisperse emulsion or heterodisperse emulsion. Each droplet in the emulsion may contain, or contain on average, 0-1,000 or more binding moiety carriers. For instances, a given droplet may contain 0, 10, 20, 30, 40, 50, 100, 200, 300, 400, 500 or more binding moiety carriers.

In certain instances, the droplet may include one or more cells from a population of cells having been infected with phage library, such that the cells secrete a clonal population of binding moiety carriers into the droplet. In particular embodiments, a given droplet may contain 0, 1, 2, or 3 cells capable of secreting a clonal population of binding moiety carriers. On average, the droplets of an emulsion of the present in invention may contain 0-3 cells capable of secreting a clonal population of binding moiety carriers, such as 0, 1, 2, or 3 cells capable of secreting a clonal population of binding moiety carriers, as rounded to the nearest whole number. In some embodiments, the number of cells capable of secreting a clonal population of binding moiety carriers in each emulsion droplet, on average, will be 1, or between 0 and 1, or between 1 and 2.

The emulsion of the present invention may include various compounds, enzymes, or reagents in addition to the capture complex and emulsion media of the present invention. These additives may be included in the emulsion solution prior to emulsification. Alternatively, the additives may be added to individual droplets after emulsification.

Clonal Binding Moiety Carrier Populations

In certain embodiments of the present invention, a clonal population of binding moiety carriers is present in an emulsion droplet with one or more antigen carriers. In particular, the emulsification may include cells having been infected with a phage library including nucleic acids encoding binding moieties, such that, once emulsified, bacteria secrete clonal phage particle binding moiety carriers into the droplets in which they are encapsulated (see, e.g., Buhr et al., Use of micro-emulsion technology for the directed evolution of antibodies *Methods* 58(1): 28-33, which is herein incorporated by reference).

Identification of Cognate Binding Moieties

The methods of the present invention include the emulsification of one or more antigen carriers and one or more binding moiety carriers in a single emulsion. Emulsification results in the compartmentalization of one or more of the antigen carriers in an emulsion droplet with one or more of the binding moiety carriers. An emulsion of the present invention will typically include a plurality of droplets, each droplet including one or more antigen carriers and one or more binding moiety carriers. The emulsion is incubated in a manner sufficient to allow binding of one or more of the cell-displayed antigens with a cognate binding moiety present in the same emulsion droplet, thereby generating one or more cognate complexes.

A variety of techniques may be employed to determine the identity of one or more binding moieties having bound an antigen carrier in an emulsion of the present invention. In certain embodiments, the emulsion is broken. Optionally, the cells are washed after the emulsion is broken. Methods of washing cells are known in the art. Cognate complexes are then isolated from unbound binding moiety carriers, unbound antigen carriers, and any other reagents not present in a cognate complex.

In particular embodiments, the broken emulsion is contacted with one or more labels. A label may be a label capable of binding one or more binding moiety carriers, but not substantially capable of binding other carriers or reagents present in the reaction. Alternatively, a label may be a label capable of binding one or more antigen carriers, but not substantially capable of binding other carriers or reagents present in the reaction. In some instances, a first label specific to the binding moiety carriers and a second label specific to the antigen carriers will be contacted with or included in the emulsion. A label of the present invention that is specific to the binding moiety carriers or antigen carriers may bind the binding moiety or antigen directly or may bind a different moiety present in binding moiety or antigen carriers. A label may itself be a binding moiety. The label may include a binding moiety and a tagging moiety that detectably labels cells. The label may tag cells with an affinity reagent, such as biotin or avidin, a fluorescent moiety, or a radioactive moiety. In instances in which the label includes a fluorescent moiety, labeled cells may be isolated by FACS. In particular instances in which both binding moiety carriers and antigen carriers are detectably labeled, they can be differentially labeled. For instance, they may be tagged by fluorescent proteins that fluoresce at distinct wavelengths.

In other embodiments, the broken emulsion is contacted with an agent that induces expression of a cell product responsible for a detectable phenotype by one or more binding moiety carriers, one or more antigen carriers, or both. The detectable phenotype may be, e.g., a fluorescent protein. In such instances, labeled cells may be isolated by FACS. In particular instances in which both binding moiety carriers and antigen carriers are detectably labeled, they can be differentially labeled. For instance, they may be tagged by fluorescent proteins that fluoresce at distinct wavelengths.

In still other embodiments, one or more of the binding moiety carriers or antigen carriers, or both, may constitutively express a protein that results in the detectable labeling of the expressing cell. For instance, one or more of the binding moiety carriers or antigen carriers, or both, may constitutively express a fluorescent protein. In such instances, labeled cells or complexes including the cells may be isolated by FACS. In particular instances in which both binding moiety carriers and antigen carriers are detectably labeled, they can be differentially labeled. For instance, they may be tagged by fluorescent proteins that fluoresce at distinct wavelengths. Numerous inducible and constitutive detectable cell phenotypes, including, e.g., antibiotic resistance, and techniques for their application are known in the art.

In certain embodiments, the strength of the label will be indicative of the affinity or avidity of one or more cognate binding moieties present in a complex of the present invention. For instance, a label that binds binding moieties or binding moiety carriers, e.g., a label that specifically binds binding moiety carriers, may bind a first complex including a certain number of binding moiety carriers in greater numbers than the same label binds a second complex including a smaller number of binding moiety carriers. In such instances, the signal detected as a result of the labeling of the first complex may be greater than the signal detected as a result of the labeling of the second complex, i.e., the strength of the signal relates to the interaction of the binding moiety carriers and antigen carriers. In particular instances in which the label is a fluorescent label, the degree of fluorescence may be indicative of the affinity or avidity of a cognate binding moiety with respect to an antigen. In particular instances, variation in levels of signal may be differentiated by FACS.

Any of the above labels may be used to isolate cognate complexes of the present invention, thereby isolating not only a cognate binding moiety of an antigen displayed by the antigen carrier of the isolated cognate complex, but also a nucleic acid encoding the binding moiety. In some instances, cognate complexes will be cultured in a non-selective media, i.e., a media permissive of the reproduction of both antigen carriers and binding moiety carriers. In other instances, the cognate complexes will be cultured in a selective media, i.e., a selective media permissive of the reproduction of only one or more antigen carriers or only one or more binding moiety carriers. In particular embodiments, the selective media may be permissive of the reproduction of only binding moiety carriers. A selective media may be, e.g., a media that includes one or more antibiotics and/or toxins, and/or lacks one or more metabolites. In such instances, the cells that are able to reproduce will be those having one or more constructs conferring antibiotic and/or toxin resistance, or the ability to synthesize the absent metabolite. In some instances, two or more complexes will be present in a single compartment of media. In certain instances, a plurality of cognate complexes will be intentionally pooled in a single compartment of media. In other instances, single cognate complexes will be isolated in individual compartments of media. The media may be a solid media, such as an agar media, or a liquid media, such as Luria broth. Various media are known in the art, as are methods and constructs for selective growth on media.

At any point subsequent to the breaking of the emulsion, the complexes can be washed one or more times. In certain embodiments, a wash removes unbound binding moiety carriers and/or unbound antigen carriers from a population of binding moiety carriers and antigen carriers, e.g., a population including one or more complexes of binding moiety and antigen carriers. In particular embodiments, one or more wash steps occur prior to the addition of a label. In other embodiments, one or more wash steps occur subsequent to the addition of a label.

The nucleic acid encoding an antigen or cognate binding moiety of the present invention may be optionally cloned or sequenced by any method known in the art. Methods of cloning and sequencing are well known in the art, including methods of deep sequencing and NextGeneration sequencing. Sequencing may include next generation sequencing technologies, such as Hyseq2500, Ion Torrent sequencing, Illumina sequencing, 454 sequencing, SOLID sequencing, or nanopore sequencing. Additional methods of sequencing are known in the art. A nucleic acid encoding an antigen or cognate binding moiety of the present invention may be sub-cloned into an expression vector for protein production, e.g., an expression vector for production of binding moieties in *E. coli* cells. Produced binding moieties may be purified, e.g., by affinity chromatography. In embodiments in which a binding moiety includes one or more fragments substantially similar to an antibody or antibody fragment, the fragments may be incorporated into known antibody frameworks for expression. For instance, if a binding moiety is an scFv, the heavy and light chain sequences of the scFv may be cloned into a vector for expression of those chains within an IgG molecule.

In any embodiment or step of the present invention, a population of binding moieties or binding moiety carriers may be subjected to a subtractive step. For instance, a population of binding moiety carriers may be subtracted against a population of cells lacking an antigen against which the population will be subsequently screened or against which the population has been previously screened.

Binding moieties or binding moiety carriers that bind the cells lacking the specified antigen will be removed from the population (i.e., subtracted), thereby removing from the population binding moieties that are not specific to the specified antigen. In certain embodiments, a population of binding moieties or binding moiety carriers is subjected to two or more rounds of subtraction. Two or more rounds may include subtraction against the same cell type or different cell types. In other instances, the cells display the specified antigen, but the specified antigen is masked during or prior to contact with the binding moieties or binding moiety carriers by the addition of a blocking agent, such as an antibody known to bind a displayed epitope, prior to subtraction. Methods of subtraction are known in the art.

In any embodiment or step of the present invention, protease inhibitors may be included to prevent degradation of displayed binding moieties and/or antigens.

Validation and Affinity Maturation of Identified Binding Moieties

One or more binding moieties identified by a method of the present invention can be further assayed to validate antigen binding, assayed to determine antigen binding characteristics, or modified to enhance one or more antigen binding characteristics, e.g., by affinity maturation. Methods of binding moiety validation, assessment, and affinity maturation are known in the art. In some instances, binding moieties identified by the methods of the present invention are modified to increase particular binding properties by methods known in the art. For instance, it is beneficial for particular applications that a binding moiety have a $K_D$ less than 10 nM. In some instances, affinity maturation will include utilization of one or more binding moieties identified by a method of the present invention as a starting reagent in a further iteration of biopanning by a method of the present invention. In other instances of affinity maturation, one or more binding moieties identified by a method of the present invention are utilized as a starting reagent in a traditional method of biopanning.

In particular instances, increasingly stringent wash conditions or biopanning conditions may be used to select for binding moieties having a desired affinity or avidity for a target antigen or antigen carrier. For instance, the density of antigen carriers may be reduced, a blocking agent may be contacted to the antigen carriers prior to or after contacting the antigen and binding moiety carriers, or the amount of detergent in one or more washes may be increased. Each of these modifications may be implemented individually or in any combination and may be applied at a single level, at escalating levels, or at depreciating levels. Any or all of these modifications can be implemented in a method of the present invention or, in some instances, in combination with other methods of biopanning known in the art, such as ELISA. These modifications are applicable to subtractive steps as well as steps in which a specified antigen is present.

EXAMPLES

The below examples include specific embodiments of the present invention. It is understood that the cells, cell membrane epitopes, binding moieties, and isolation techniques presented below are for exemplary purposes and can include, e.g., those embodiments disclosed within the claims.

Example 1

Screening an scFv Phage Library by Biopanning Against Whole Cells in a Micro-Emulsion We have previously developed an approach utilizing water-in-oil emulsion to isolate cells secreting phage particles that display desirable scFvs (Buhr et al., 2012. Use of micro-emulsion technology for the directed evolution of antibodies. *Methods* 58: 28-33). In this previously developed method, a large library of antibody-displaying phage will bind to antigen-coated beads in individual compartments. The methods of the present invention further provide a micro-emulsion approach to biopanning phage against whole cells, e.g., 293-F cells over-expressing the integral membrane protein Slc7A11 (xCT). Significantly, the present invention features biopanning against cells displaying membrane protein antigens, rather than biopanning against antigen-coated beads. Rather than biopanning a large, mixed population in bulk, present methods allow individually querying of clonal populations of phage against an antigen, with subsequent identification of cognate binding moieties of the antigen by Fluorescence Activated Cell Sorting (FACS).

The use of emulsions to generate microdroplets offers advantages for cell-based panning. Smaller volumes, i.e., fewer cells, are required, and it may be possible to identify cognate binding moieties specific to a particular antigen from a single round of selection (Kiss et al., 2011. Phage ESCape: an emulsion-based approach for the selection of recombinant phage display antibodies. *J. Immunol. Methods* 367: 17-26). Since emulsified antigen carriers are compartmentalized in droplets with clonal populations of antibody-displaying phage, the number of binding moiety carriers bound to an antigen carrier can be indicative of affinity and/or avidity. In particular, binding moieties with greater affinity and/or avidity for one or more antigens displayed by an antigen carrier present in the same droplet will bind that antigen carrier in greater numbers than binding moieties having lower affinity and/or avidity for an antigen carrier present in the same droplet. Steps of screening an scFv phage library by biopanning against whole cells in a micro-emulsion are further described below.

Example 2

Preparation and Validation of Target Antigens

The methods of the present invention are applied to the identification of scFv binding moieties capable of binding the integral membrane protein Slc7A11 (xCT). xCT is the core subunit of the dimeric system $x_c^-$ high affinity cysteine transporter, which belongs to a family of heteromeric amino acid transporters (HATs). These transporters are composed of a heavy subunit and a light subunit coupled via a disulfide bridge. The heavy subunit is involved in trafficking the heterodimer to the plasma membrane, while the light subunit confers transport and substrate specificity. xCT is a light chain subunit, while the heavy chain subunit of system $x_c^-$ is 4F2hc, which is highly glycosylated. xCT proteins are identified, e.g., in humans, macaques, and mice. In the present example, scFv binding moieties that recognize different epitopes of the displayed portion(s) of xCT are generated.

Because xCT is a 12 transmembrane domain protein with N- and C-termini located inside the cell, it would be difficult to generate antibodies that recognize the extracellular loops of the protein by conventional screening approaches, such as screening candidate binding moieties against recombinant xCT protein or peptides. Instead, the present invention features, e.g., developing cell lines over-expressing the xCT subunit of system $x_c^-$ and employing the over-expressing cells as antigen carriers.

TABLE 1

| | xCT proteins | | |
|---|---|---|---|
| Species | Uniprot Accession No. | % Identical to Human | Size (residues) |
| Homo sapiens | Q9UPY5 | n/a | 501 |
| Macaca fascicularis | G7P6A5 | 98 | 501 |
| Mus musculus | Q9WTR6 | 89 | 502 |

HEK-293 Cells Over-Expressing Human xCT To generate HEK-293 cells over-expressing human xCT, xCT is amplified by PCR from the cDNA clone (DNASU HsCD00399924) and sub-cloned into the pCDNA3.1 expression vector (Life Technologies). FreeStyle 293-F cells (Life Technologies, R790-07), which are adapted from the HEK-293 cell line for suspension growth in serum-free medium, are transiently transfected with the expression construct. Five to seven days post-transfection, the cells are harvested, washed, and incubated with a commercial FITC-conjugated anti-xCT polyclonal antibody (Abcam, ab37815). The cells are analyzed by immunofluorescence and FACS for over-expression of xCT.

HEK-293 Cells Over-Expressing Mouse and Macaque xCT

*Mus musculus* xCT is 89% identical to its human homolog (Table 1). To ensure that scFvs identified in the screen cross-react with mouse xCT, mouse xCT (Accession #AB022345) is synthesized and the cDNA is cloned into pCDNA3.1 as described above. 293-F cells are transiently transfected with this expression construct. Cells expressing mouse xCT are used for a QC assay of the cross-reactivity of identified binding moieties.

*Macaca fascicularis* (cynomolgus monkey) xCT is 98% identical to the human protein (Table 1) and the amino acid differences are in the cytoplasmic or transmembrane domains rather than the extracellular domains. Hence, the antibodies raised against human xCT are expected to react fully with the cynomolgus monkey protein. Macaque xCT is cloned, expressed, and used in a QC assay as described above.

HEK-293 Cells Over-Expressing Slc7A9

Slc7A9 is the light subunit of another heteromeric amino acid transporter associated with the 4F2hc heavy subunit (Wittrup, K. D. 2001. Protein engineering by cell surface display. *Curr. Opin. Biotechnol.* 12: 395-399; Shih, A. Y., Murphy, T. H. 2001. xCT Cystine Transporter Expression in HEK293 Cells: Pharmacology and Localization. *Biochem. Biophys. Res. Commun.* 282: 1132-1137; Lo et al., 2008. The $x_c^-$ Cystine/Glutamate Antiporter: A Potential Target for Therapy of Cancer and Other Diseases. *J. Cell Physiology* 215: 593-602). Cells over-expressing Slc7A9 are used for subtraction of the phage library against clones recognizing 4F2hc alone or another displayed protein on the 293-F cells. Slc7A9 is amplified by PCR from the cDNA clone (DNASU, HsCD00040957) and sub-cloned into the pCDNA3.1 expression vector. FreeStyle 293-F cells are transiently transfected with this expression construct as above.

Optimization of xCT Over-Expression

Figure 1:
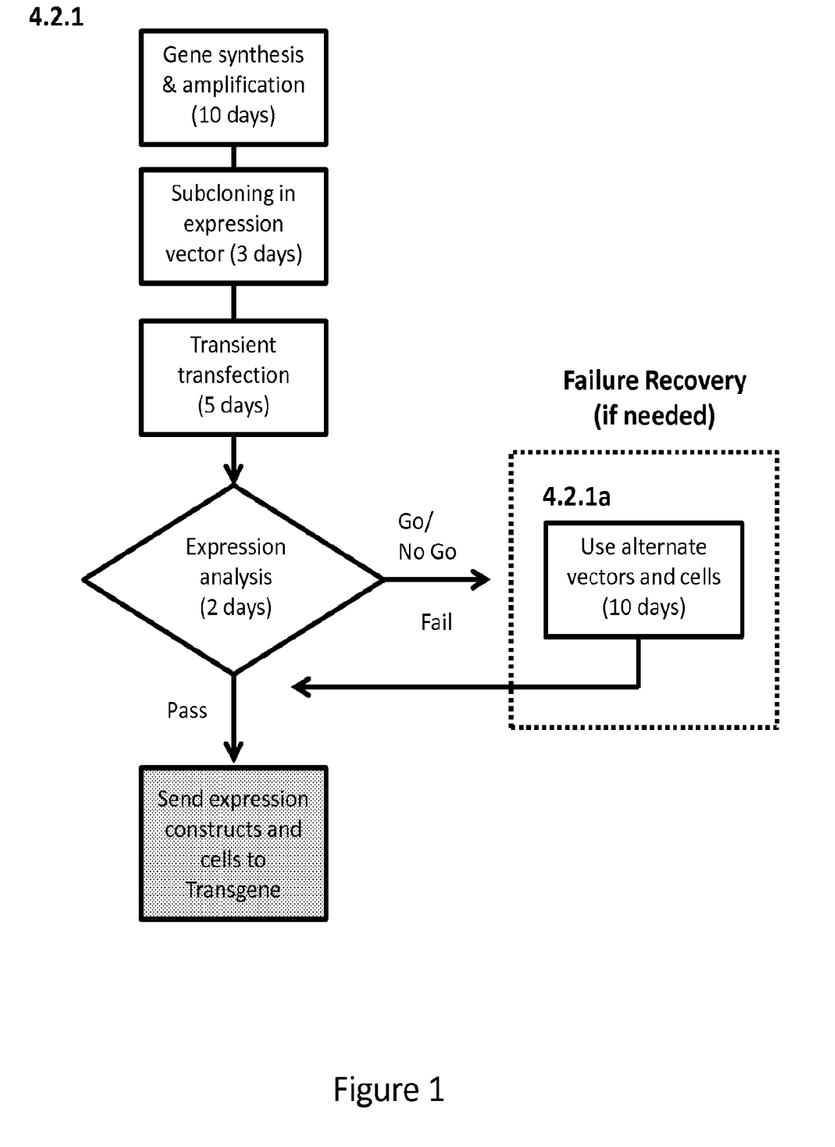

Beyond HEK-293 cells, over-expression of xCT alone has been shown to robustly increase xCT activity in, NIH3T3 fibroblasts, murine hippocampal HT22 cells, and astrocytes (Lewerenz et al., 2012. The Cystine/Glutamate Antiporter System $x_c^-$ in Health and Disease: From Molecular Mechanisms to Novel Therapeutic Opportunities. *Antioxidants and Redox Signaling*). Over-expression in these other cell lines is performed and evaluated. Alternative vectors include regulated mammalian expression systems (e.g., pF12A RM Flexi Vector, Promega) are also evaluated (see, e.g., FIG. 1).

Optimization of Recognition of xCT by Binding Moieties on the Cell Surface of xCT Over-Expressing Cells A polyclonal antibody known to detect xCT over-expression by a control cell line in a manner detectable by a FACS-based assay is used to determine whether the over-expression lines generated in examples 3 to 6 enable recognition of xCT on the cell surface (Pampliega, O. et al., 2011. Increased Expression of Cystine/Glutamate Antiporter in Multiple Sclerosis. *J. Neuroinflammation* 8:63). The known polyclonal antibody can be commercial polyclonal anti-xCT antibody (Abcam,111822), which recognizes an extracellular epitope of xCT. If this antibody fails to detect xCT in control or over-expression cell lines by FACS- or immunofluorescence-based assays, membrane fractions can be prepared and Western blots performed, for which purpose several antibodies are known in the art. Further, Transgene (or a third party recommended by Transgene) can conduct an $_L$-[$^3$H]-glutamate uptake assay (Molek, P., Strukelj, B., Bratkovie, T. 2011. Peptide phage display as a tool for drug discovery: targeting membrane receptors. *Molecules* 16, 857-887) to confirm up-regulation of xCT in these cells. The control cell line can be a human cell line, as xCT is induced in most cultured human cell lines. xCT is over-expressed by 5 fold or more in some cultured human cell lines. In additional trials, the known xCT binding moiety is added to the control cells to block xCT.

Optimization of xCT Over-Expressing Cells for Use in Emulsions

Figure 3:
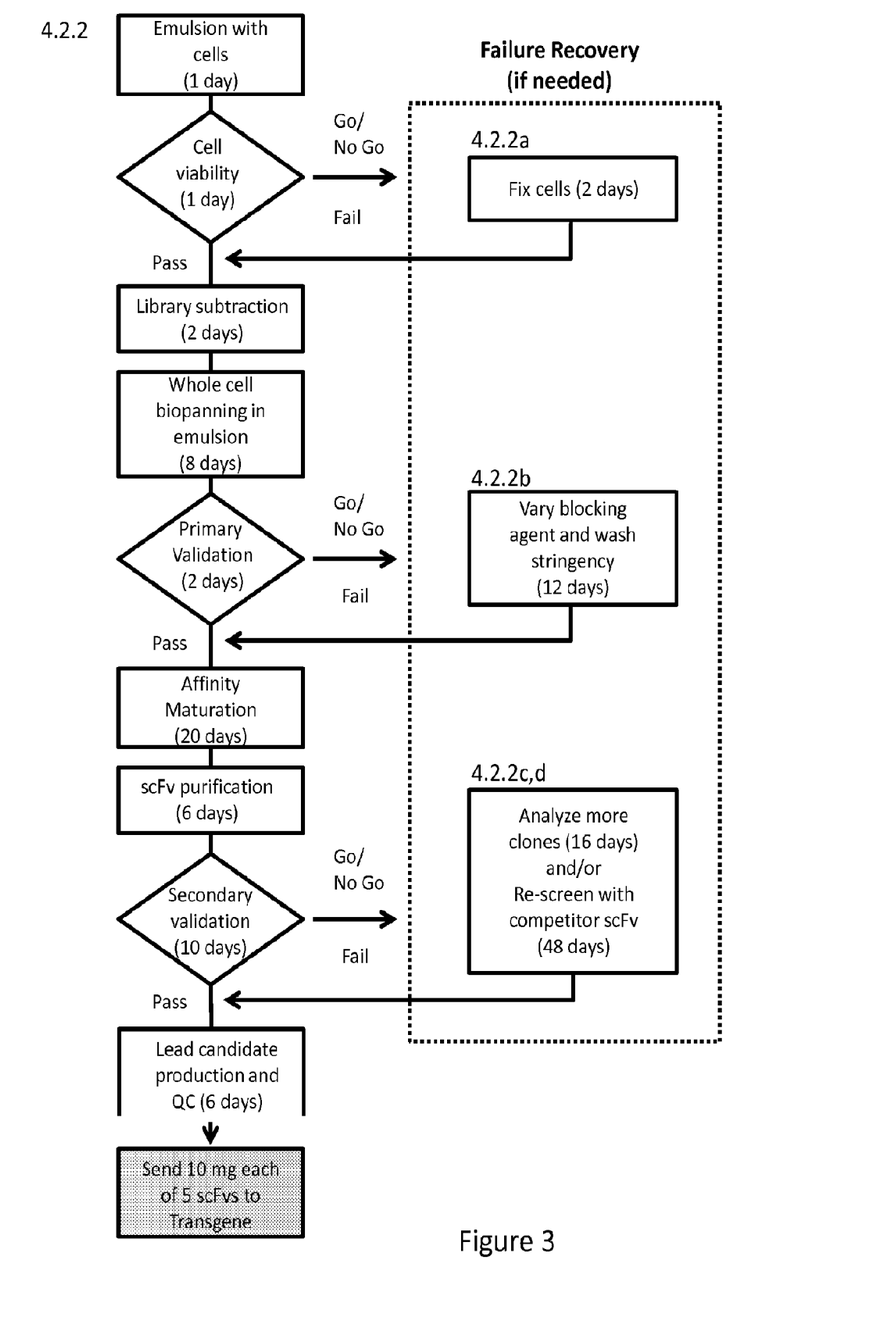
Figure 4:
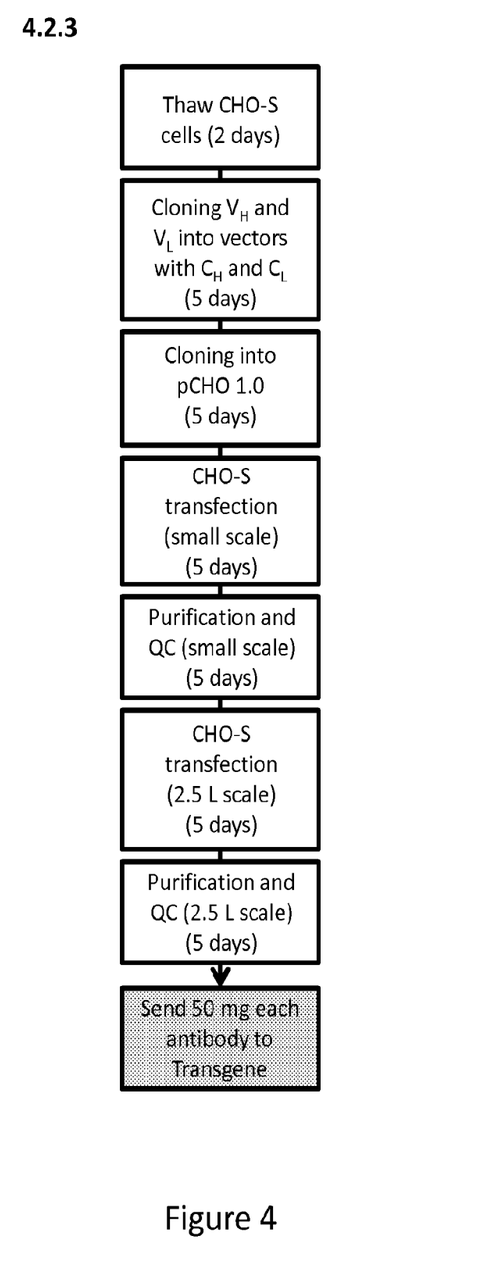

Cell lines over-expressing xCT are evaluate for survival in emulsion. Mammalian cells have been shown to survive up to 4 days following encapsulation in perfluorocarbon oils (Brouzes et al., 2009. Droplet microfluidic technology for single-cell high-throughput screening. *Proc. Natl. Acad. Sci. USA* 106: 14195-14200). Other oil/surfactant mixtures (e.g., silicone oils) are sampled if needed. Alternatively, cells can be fixed, for example, with formaldehyde (FIG. 3). Fixed cells in suspension have been used successfully for whole cell biopanning (Tate, C. G. 2001. Overexpression of mammalian integral membrane proteins for structural studies. *FEBS Lett.* 504, 94-98).

Example 3

Figure 2:
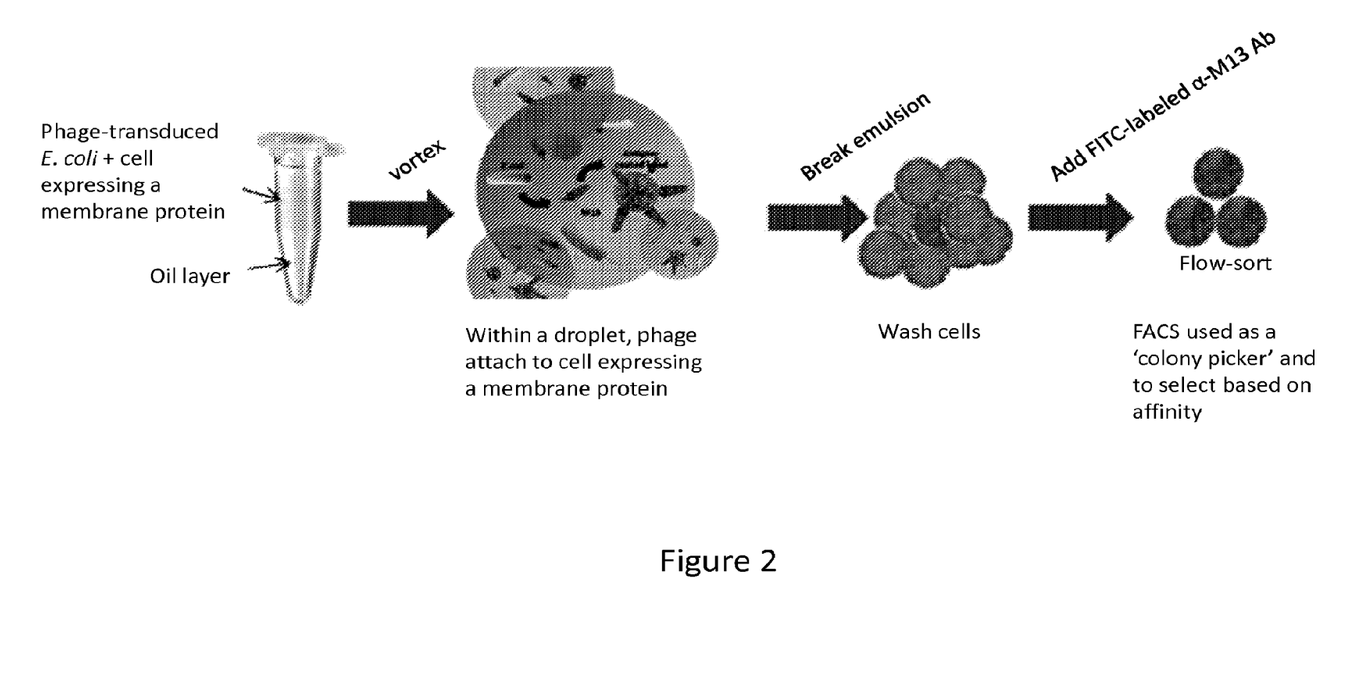

Screening of Human scFv Library by Whole Cell Phage Biopanning in Micro-Emulsions A micro-emulsion approach is used in whole cell phage biopanning to screen for binding moieties capable of binding 293-F cells over-expressing xCT. In our previous studies using water-in-oil emulsion methods (Buhr et al., 2012. Use of micro-emulsion technology for the directed evolution of antibodies. *Methods* 58: 28-33), a large library of antibody-displaying phage was contacted with antigen-coated beads in individual compartments. The method allows clonal populations of amplified phage to be individually queried against selected antigens with subsequent identification of cognate binding moieties by Fluorescence Activated Cell Sorting (FACS). Here, the antigen-coated bead of our previous studies is replaced with an antigen carrier of the present invention (FIG. 2).

The biopanning for cognate binding moieties of xCT will utilize an emulsion. Emulsions are provide certain advantages in biopanning, including the ability to conduct experiments using smaller volumes (fewer cells) and the possibility of identifying cognate binding moieties from a single round of selection (Kiss et al., 2011. Phage ESCape: an emulsion-based approach for the selection of recombinant phage display antibodies. *J. Immunol. Methods* 367: 17-26). Since clonal populations of the binding moiety carrier are contacted with the antigen carrier within droplets, the number of binding moiety carriers bound to an antigen carrier can be indicative of affinity and/or avidity, permitting discrimination of high affinity binders by FACS.

Subtractive Purification

Due to the complexity of the plasma membrane, it may be desirable to remove phage that recognize proteins other than xCT on the surface of 293-F cells. Hence, in some embodiments, the library can be subtracted by one or two rounds of biopanning against non-transfected or Slc7A9 vector-transfected cells. This may be important in the case of xCT because the 4F2hc heavy chain is associated with other amino acid transporters and is not specific for xCT. Subtraction against, e.g., Slc7A9 vector-transfected cells or untransfected cells should reduce the likelihood of identifying scFvs recognizing 4F2hc alone or other changes to the cell surface induced by the stress of protein over-expression.

In the present example, subtractive purification precedes selection for cognate binding moieties of xCT. Phage displaying binding moieties that are not removed from the binding moiety pool during this purification step are transduced to susceptible *E. coli* and amplified. Optionally, a known xCT binding moiety is added to cells prior to subtraction of the library in order to block xCT.

Biopanning Against Whole Cells in Emulsion to Identify Cognate Binding Moieties of xCT

*E. coli* transduced by phage after subtractive purification of the phage library are emulsified with xCT vector-transfected 293-F cells (i.e., xCT over-expressing cells) in perfluorocarbon oil following the protocol established previously (Buhr et al., 2012. Use of micro-emulsion technology for the directed evolution of antibodies. *Methods* 58: 28-33) to generate droplets of approximately 100 μm diameter. The emulsified cells and phage are incubated according to standard 293-F growth procedure known in the art. After overnight incubation, the emulsion is broken, and the aqueous layer is removed. The cells are washed, e.g., with PBS (with or without detergent), and a FITC-labeled anti-M13 antibody (Acris Antibodies) is added. This label will result in the fluorescent tagging of binding moiety carriers and, consequently, the tagging antigen carriers having been bound by one or more binding moiety carriers. The fluorescent population is sorted on a BD FACS Aria. Bound phage are eluted and recovered by infection of mid-log phase TG1 cells. This process is optionally repeated for further enrichment.

Affinity Maturation of Binding Moieties Identified by Biopanning Against Whole Cells in Emulsion Cognate binding moieties of xCT cloned or sequenced following biopanning against whole cells in emulsion are affinity matured using mutagenesis followed by, e.g., conventional whole cell phage biopanning against the xCT over-expressing cells under stringent selection conditions. In order to isolate the scFvs with highest affinity or avidity, the cell density may be reduced, the wash stringency may be increased, and blocking agent may be added in each progressive round of selection. Different blocking agents can be used, such as casein or BSA. Wash stringencies may be varied by varying the number of washes or the amount of detergent (e.g., 0.05-0.5% Tween-20) in the wash buffer in order to eliminate non-specific binders (See FIG. 3). Protease inhibitors can be added to the media at any step to prevent degradation of the scFv displayed on the phage. The ratios of phage-transduced *E. coli* cells to 293-F cells can be, e.g., altered in the droplets to allow optimal detection of binding by FACS.

Example 4

Validation and Synthesis of Identified Binding Moieties

The scFv binding moieties identified and optionally affinity matured as described in example 2 are further validated.

Validation of Specificity by Non-Competitive ELISA

Individual phage clones are screened by ELISA against immobilized, fixed 293-T cells that over-express the target antigen, xCT. The binding moieties are also validated by ELISA against immobilized, fixed 293-Tcells that over-express Slc7A9, immobilized, fixed 293-Tcells that over-express mouse xCT, and immobilized, fixed 293-Tcells that have not been engineered to over-express an xCT protein or other protein of the present invention. ELISA against the cells over-expressing Slc7A9 and ELISA against cells that do not over-express a protein of the present invention provide negative controls. Binding moieties that bind xCT over-expressing cells with substantially greater affinity or avidity than negative controls will be referred to as xCT-specific.

Nucleic acids encoding scFv binding moieties that are positive in the ELISA assay against cells over-expressing xCT, but negative in ELISA against cells over-expressing Slc7A9, are amplified by PCR and sequenced. Unique hits are sub-cloned into an expression vector for protein production. The expression vector is cloned into *E. coli* for expression of the encoded scFv binding moieties, and the binding moieties are purified by affinity chromatography.

Binning of Binding Moieties Based on Competitive ELISA

Competition ELISA using pairs of xCT-specific scFvs against immobilized, fixed xCT over-expressing 293-F cells are conducted to determine whether different antibodies recognize different epitopes of xCT. Binding moieties may be systematically binned on the basis of results of competitive ELISA assays.

If all of the selected scFv binding moieties identified are found to recognize a single epitope, it is desirable to identify clones targeting other epitopes as well. This may be accomplished by further analyzing addition binding moieties not yet assayed by competitive ELISA (See FIG. 3). Alternatively, or in addition, the emulsion screen can be repeated using an scFv against the epitope recognized by the obtained binding moieties, such as one of the obtained binding moieties, as a competitor to block that epitope on the cells during the screen (See FIG. 3). Alternatively, or in addition or combination, if none of the scFvs cross-react with mouse xCT, the screen can be repeated using human and mouse cell lines in alternate rounds.

Example 5

Integration of scFv Binding Moiety Fragments into IgG Molecules

IgG heavy chains ($V_H$) and light chains ($V_L$) present in selected xCT-specific scFv sequences are amplified by PCR. The $V_H$ and $V_L$ sequences are cloned into vectors expressing the constant regions of the heavy and light chains (InvivoGen cat # pFUSE2ss-CHIg-hG1 and pFUSE2ss-CLIg-hl2). These expression vectors have the IL-2 signal sequence for extracellular excretion of expressed protein. The IgGs expressed using this system are purified from growth media.

After sequence verification, the heavy and light chains are amplified from the appropriate expression vectors and cloned into the Freedom pCHO 1.0 expression vector.

Other Embodiments

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. A method of isolating a binding moiety specific to a cell-membrane bound epitope, said method comprising:
   a. providing an emulsion with a plurality of droplets, wherein each of said droplets comprises:
      (i) a plurality of antigen carriers displaying said cell-membrane bound epitope, and
      (ii) a plurality of binding moiety carriers,
   wherein the one or more said antigen carriers comprises an animal cell, and wherein the plurality of said binding moiety carriers comprise a phage displaying a binding moiety and comprising a nucleic acid that encodes the binding moiety, the phage being released into said droplets by phage-transduced E. coli;
   wherein, within said droplets, one or more of said antigen carriers displaying said cell-membrane bound epitope contacts a plurality of said binding moiety carriers; and
   wherein, if an individual binding moiety is specific to said antigen carrier present in the same droplet, said contacting results in a complex, the complex comprising at least one binding moiety bound to a membrane of an intact binding moiety carrier and at least one antigen bound to a membrane of an intact antigen carrier;
   b. breaking said emulsion;
   c. washing said complexes;
   d. adding a labeled binding agent specific for said binding moiety carrier to said washed complexes resulting in said complexes being labeled; and
   e. isolating said labeled complexes;
   wherein said isolation of step e results in the isolation of a binding moiety specific for said cell-membrane bound epitope and said nucleic acid that encodes the binding moiety.

2. The method of claim 1, wherein said phage of said binding moiety carrier is an M13 bacteriophage, lambda phage, T4 phage or T7 phage.

3. The method of claim 1, wherein the binding moiety comprises a DARPin, FN3 (fibronectin repeats), Fork-head associate protein, scFv, Fab, or other antibody-derived protein.

4. The method of claim 1, further comprising repeating steps a-e with a plurality of binding moieties isolated in step e.

5. The method of claim 1, wherein said labeled binding agent comprises a fluorescent label.

6. The method of claim 1, wherein said cell-membrane bound epitope is natively expressed by said animal cells.

7. The method of claim 1, wherein said plurality of binding moiety carriers of step a are generated by contacting cells not having said cell-membrane bound epitope with a plurality of binding moiety carriers and isolating the subset of said binding moiety carriers that fail to bind said cells not thereby forming a mixture of binding moiety carriers that failed to bind said having said cell-membrane bound epitope, thereby generating said plurality of binding moieties of step a of claim 1.

8. The method of claim 1, wherein the emulsion is a monodispersed emulsion.

9. The method of claim 1, wherein the emulsion is a heterodispersed emulsion.

10. The method of claim 5, wherein said isolation of step e occurs by fluorescent activated cell sorting (FACS).

11. The method of claim 1, wherein said cell-membrane bound epitope is recombinantly expressed by said animal cells.

* * * * *

UNITED STATES PATENT AND TRADEMARK OFFICE
CERTIFICATE OF CORRECTION

PATENT NO. : 10,011,655 B2  
APPLICATION NO. : 14/652385  
DATED : July 3, 2018  
INVENTOR(S) : Michael Weiner et al.

Page 1 of 1

It is certified that error appears in the above-identified patent and that said Letters Patent is hereby corrected as shown below:

On the Title Page

Under ABSTRACT, Line 3, replace "eptiopes" with --epitopes--.

In the Specification

Column 5, Line 15, delete "human".

Column 18, Line 31, replace "evaluate" with --evaluated--.
  Line 64, replace "are provide" with --provide--.

In the Claims

Column 22, Lines 32-33, in Claim 7, delete "thereby forming a mixture of binding moiety carriers that failed to bind said".

Signed and Sealed this  
Thirtieth Day of October, 2018

Andrei Iancu  
*Director of the United States Patent and Trademark Office*